(12) United States Patent
Park et al.

(10) Patent No.: US 8,257,973 B2
(45) Date of Patent: Sep. 4, 2012

(54) METHOD FOR CO-CULTURE OF HUMAN EMBRYONIC STEM CELLS AND FIBROBLAST FEEDER CELLS USING A POLYESTER MEMBRANE

(75) Inventors: Hyun Sook Park, Seoul (KR); Sun Ray Lee, Seoul (KR)

(73) Assignee: Modern Cell & Tissue Technologies, Inc., Seoul (KR)

( * ) Notice: Subject to any disclaimer, the term of this patent is extended or adjusted under 35 U.S.C. 154(b) by 412 days.

(21) Appl. No.: 12/375,676

(22) PCT Filed: May 29, 2007

(86) PCT No.: PCT/KR2007/002597
§ 371 (c)(1), (2), (4) Date: Oct. 7, 2009

(87) PCT Pub. No.: WO2008/020675
PCT Pub. Date: Feb. 21, 2008

(65) Prior Publication Data
US 2010/0075418 A1    Mar. 25, 2010

(30) Foreign Application Priority Data
Aug. 17, 2006    (KR) .................. 10-2006-0077478

(51) Int. Cl.
C12N 5/02    (2006.01)
C12N 5/00    (2006.01)
C12N 5/071    (2010.01)
(52) U.S. Cl. ......................... 435/373; 435/366
(58) Field of Classification Search .............. 435/373, 435/366
See application file for complete search history.

(56) References Cited

U.S. PATENT DOCUMENTS 5,578,492 A * 11/1996 Fedun ................... 435/297.5
6,730,513 B1    5/2004 Hunziker et al.
2005/0106725 A1    5/2005 Palecek et al.
2005/0164377 A1    7/2005 Miyabayashi et al.
2005/0244961 A1    11/2005 Short et al.
2008/0003676 A1 * 1/2008 Sheridan et al. .............. 435/354

FOREIGN PATENT DOCUMENTS

JP    2005-130838 A    5/2005
JP    2007-164817 A    6/2007

OTHER PUBLICATIONS

Millipore, "Millicell® cell culture and Insert Plates", pp. 1-8, 2006.*
Corning. "Cell Culture Selection Guide," pp. 1-18, 2002.*
Conley et al., "Mouse Embryonic Stem Cell Derivation and Mouse and Human Stem Cell Culture and Differentiation as Embryoid Bodies," Unit 23.2, from Current Protocols in Cell Biology, 23.2.1-23.2.22, 2005.*
Office Action dated Jul. 12, 2011 of corresponding Japanese Patent Application 2009-524545—3 pages.
Benjamin E. Reubinoff et al., Embryonic stem cell lines from human blastocysts: somatic differentiation in vitro; Nature Biotechnology, Apr. 2000, vol. 18, No. 4, pp. 399-404.
Thomson et al., (1988), "Embryonic Stem Cell Lines Derived from Human Blastocysts", Science, vol. 282(5391): 1145-7.
Smith, A.G., (2001), "Embryo-derived stem cells: of Mice and Men", Annu. Rev. Cell Dev. Biol. vol. 17:435-462.

* cited by examiner

Primary Examiner — Thaian N Ton
(74) Attorney, Agent, or Firm — Knobbe, Martens, Olson & Bear, LLP

(57) ABSTRACT

The present invention relates to a method for co-culture of stem cells using feeder cells, more particularly to a method for culturing stem cells by using a membrane having a number of pores to separate stem cells and feeder cells. In the present invention, the culture condition of stem cells optimized is provided, in which stem cells and feeder cells are cultivated independently in separate spaces while permeating essential substances selectively. The stem cells prepared in the present invention continue to remain indifferent and be supported by feeder cells until needing being sub-cultured. In addition, the stem cells even for therapeutic use can be obtained without any contaminant since not pretreated with a cytostatic agent such as mitomycin or irradiated. Therefore, the method for co-culturing stem cells by using a membrane of the present invention can be widely used for clinical applications.

6 Claims, 19 Drawing Sheets

Con : Control group
Styr : Polystylene
Est : Polyester
Cab : Polycarbonate
Col : Collagen-coated polytetrafluoromethylene Con : Control group
Styr : Polystylene
Est : Polyester
Cab : Polycarbonate
Col : Collagen-coated polytetrafluoromethylene Con = Control group
Est = Polyester
Tcon = Polyester(2 passages) +Control group

METHOD FOR CO-CULTURE OF HUMAN EMBRYONIC STEM CELLS AND FIBROBLAST FEEDER CELLS USING A POLYESTER MEMBRANE

This application is U.S. National Phase of International Application PCT/KR2007/002597, filed May 29, 2007 designating the U.S., and published in English as WO 2008/020675 on Feb. 21, 2008, which claims priority to Korean Patent Application No. 10-2006-0077478, filed Aug. 17, 2006.

TECHNICAL FIELD

The present invention relates to a method for co-culture of stem cells using feeder cells, more particularly to a method for culturing stem cells by using a membrane having a number of pores to separate stem cells from feeder cells. The present invention provides an optimal condition for culturing stem cells, in which 2 kinds of cells can be cultivated independently in separate spaces while permeating essential substances selectively.

BACKGROUND ART

In 1981, mouse embryonic stem cells have been first cultured in a test tube. In 1988, this method of in vitro culture has been combined with a gene targeting technique so as to first make a transformed mouse having a targeted gene. After that, the mouse gene targeting technique plays an important role to investigate genetic functions and to build up human disease models. Further, it drives life/medical sciences to develop (Smith A. G., Annu. Rev. Cell Dev. Biol., 17: 435-62, 2001). In contrast to the mouse case, human embryonic stem cells started to be cultured in vitro in 1998, 17 years later. Dr. Thompson has first established a human embryonic stem cell in University of Wisconsin (Thomson J. A., Science 282 (5391): 1145-7, 1998). The human embryonic stem cell is more difficult to be cultured and manipulated than the mouse stem cell. Either, it is improper to be mass-cultured, even if necessary to develop therapeutic agents by performing a gene or in vitro manipulation. Therefore, it is required to complete a culture method that can proliferate stem cells effectively and control the quality easily.

The culture method popularly used is based upon the procedure Dr. Thompson established. Precisely, mouse embryonic fibroblasts are treated with mitomycin or irradiated in order to inhibit the cell growth. Then, the fibroblasts are inoculated to previously express extra-cellular substrates and cytokines embryonic stem cells need. The resulting cells are used for feeder cells, on which embryonic stem cells are inoculated. But, the optimal composition of culture medium of the stem cell is different from that of the feeder cell. To a basic medium of the embryonic stem cell, 20% serum replacement (Invitrogen Inc.) is added. In contrast, 20% fetal bovine serum (FBS) is added to a culture media of the feeder cell.

There are several disadvantages of stem cell culture. Because FBS is essential to survive fibroblasts, the fibroblast does not play a role of feeder cells when cultured with serum replacement instead of fetal bovine serum. In addition, this procedure reduces the cell survival of feeder cells to 5 to 7 days, since treating mitomycin or irradiating. In detail, stem cells should be sub-cultured before being confluent, even if they are first derived or delay a cell passage. Besides, feeder cells may not be safe due to mitomycin. Furthermore, stem cells are inevitably mixed with feeder cells when being sub-cultured, because 2 kinds of cells are cultivated on the same culture plate. This contamination causes a serious problem in case of clinical applications.

In order to settle above-mentioned problems, the present inventors have tried to co-culture stem cells with feeder cells by using a polymer membrane, in which 2 kinds of cells are cultivated in separate spaces while permeating essential substances selectively. As a result, the stem cell and the feeder cell can be cultured respectively under optimized conditions. Therefore, the present invention has been completed to provide the most optimal process for culturing stem cells successfully.

DISCLOSURE OF INVENTION

The object of the present invention is to provide a method for co-culturing stem cells and feeder cells, in which the stem cells remain indifferent (not differentiated) and the feeder cells is cultured under an optimized condition.

In order to attain the objects of the present invention, a method for culturing stem cells by using feeder cells, in which stem cells and feeder cells are cultivated in separate spaces by using a polymer membrane having a number of pores is provided.

In addition, the method for culturing stem cells, in which the polymer membrane is comprised of polyester is provided.

In addition, the method for culturing stem cells, in which the diameter of the pores is in the range of 0.2 to 0.5 μm is provided.

In addition, the method for culturing stem cells, in which the porosity of the polymer membrane is in the range of 2.0 E+06 to 6.0 E+06 is provided.

In addition, the method for culturing stem cells, in which the feeder cells are cultured under the polymer membrane and the stem cells are cultured on the polymer membrane is provided.

In addition, the method for culturing stem cells, in which the stem cells are embryonic stem cells is provided.

In addition, the method for culturing stem cells, in which the feeder cells are cultured with culture media containing serum and the stem cells are cultured with serum-free or serum-replacement media is provided.

In addition, the method for culturing stem cells, in which the feeder cells are not pretreated with any cytostatic agent is provided.

In addition, the method for culturing stem cells, in which the stem cells are sub-cultured in separate spaces by using the polymer membrane and transferred onto feeder cells subsequently is provided.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1A:
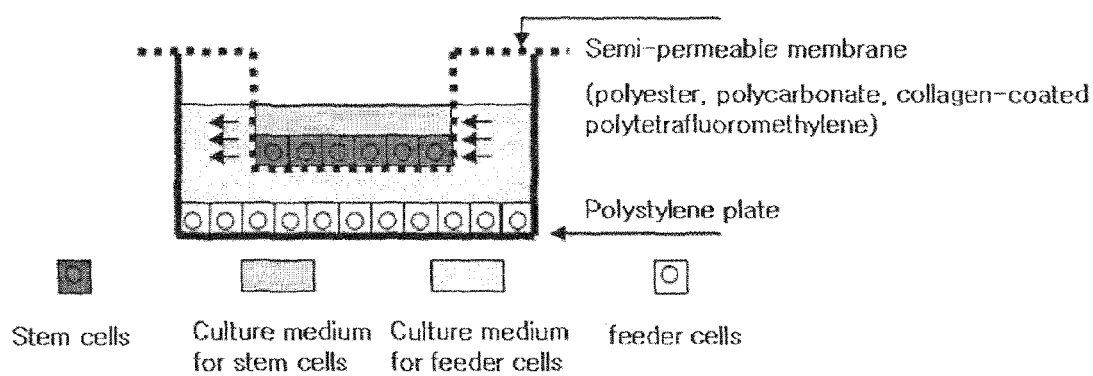
FIG. 1a depicts the schematic diagram of co-culture of stem cells using a semi-permeable membrane.

Hereinafter, the present invention will be described more clearly as follows.

The present invention provides a method for co-culturing stem cells and feeder cells effectively.

In an embodiment of the present invention, a method for culturing stem cells by using feeder cells, in which stem cells and feeder cells are cultivated in two spaces separated by a polymer membrane having a number of pores is provided.

In the present invention, the feeder cells play a role to give various nutrients and cytokines necessary for the self-renewal of stem cells and not to differentiate stem cells. Any kind of feeder cells widely used can be selected. Both fibroblasts derived from animals including mouse and fibroblasts derived from human can be utilized. In general, mouse feeder cells are so problematic to contaminate human stem cells. In the present invention, stem cells are separated from feeder cells through a polymer membrane so that pure human stem cells can be obtained while excluding animal cells.

The polymer membrane of the present invention should not have any cyto-toxicity during a co-culture. Any kind of biocompatible polymers can be selected for this use, if molded to a membrane. Preferably, the polymer material can be selected from a group comprising poly(lactic acid) (PLA), poly(glycolic acid) (PGA), poly(ethylene terephtalate) (PET), polytetrafluoroethylene (PTFE), polyurethane (PU), poly(methyl meta-acrylic acid) (PMMA), polyester, polycarbonate and the like, but it may not be limited. More preferably, the polymer material can be selected from a group comprising polyester, polycarbonate and polytetrafluoroethylene (PTFE). Most preferably, the polymer material can be a polymer material comprised of a main component of polyester. In addition, the polymer material is comprised of synthetic polymers alone or coated with gelatin, collagen or the like.

In the present invention, the pores of polymer membrane should not pass feeder cells and stem cells, but permeate bioactive molecules including growth factors of stem cells and differentiation inhibiting factors secreted from feeder cells. Preferably, the diameter of the pores is in the range of 0.1 to 1 μm. More preferably, the diameter of the pores is in the range of 0.2 to 0.5 μm.

Within the range of the pore size, bio-molecules secreted for feeder cells can permeate, but macromolecules composing culture media cannot pass. Thus, stem cells and feeder cells are not mingled so as to prevent a contamination by culture media. The polymer membrane of the present invention is called as a "semi-permeable membrane" that is different from a completely-permeable membrane passing whole cell bodies.

The porosity of polymer membrane should have a range effectively permeating bioactive molecules including growth factors of stem cells and differentiation inhibiting factors secreted from feeder cells. Preferably, the porosity of the polymer membrane is in the range of 2.0 E+06 to 6.0 E+06 that corresponds to polyester. When the porosity increases, embryonic stem cells cannot grow normally and tend to form an embryoid body. In contrast, when the porosity decreases, embryonic stem cells tend to differentiate naturally. The porosity (pore density) means the number of pores per unit square meter.

The polymer membrane of the present invention may divide a culture plate to 2 separate spaces. By a border of the polymer membrane, stem cells and feeder cells can be placed separately on any location. Preferably, the feeder cells are cultured under the polymer membrane and the stem cells are on the polymer membrane, when being divided to up- and down-positions on a culture plate. In this case, stem cells proliferate more actively and differentiate less effectively.

In the present invention, the stem cell can be selected from any kinds of stem cells including embryonic stem cell, adult stem cell and cloned stem cell for therapeutic use, if requiring feeder cells during a co-culture. Preferably, the stem cell can be embryonic stem cells including cloned stem cells. In the method for culturing stem cells of the present invention, it is natural to comprise a procedure for deriving stem cells.

In the method for culturing stem cells, preferably the feeder cells are cultivated by using culture media containing serum and the stem cells are cultivated by using serum-free or serum-replacement media. Each space of a culture plate is filled with each medium according to cell kinds. Because stem cells are usually induced to differentiate by serum, both stem cells and feeder cells should be co-cultured by using a serum-free medium. Thus, the feeder cells have to grow under an improper condition. In the present invention, the culture condition can be optimized respectively since it is divided by a polymer membrane. The culture space of stem cells is filled with a serum-free or serum-replacement medium so that it prevents stem cells from differentiation. In contrast, the culture space of feeder cells is filled with a culture medium containing serum so that it gives a most optimal environment for cells.

In the method for culturing stem cells of the present invention, the feeder cells are not pretreated with any cytostatic agent. In prior arts, the culture procedure reduced a survival period of feeder cells and may prevent the normal growth of stem cells, because treating mitomycin or irradiating onto cells. In the present invention, the culture plate is previously divided by a polymer membrane to exclude feeder cells interfering stem cells. Therefore, it needs not to pre-treat cytostatic agents and is possible to culture feeder cells in a high number. It is also able to elongate the survival period of feeder cells. Hence, stem cells need not be sub-cultured before being confluent. Stem cells can be cultured continuously for 2 weeks when first derived, not 5 to 7 days.

In particular, the method for co-culturing stem cells using feeder cells of the present invention comprises following steps: the stem cells are sub-cultured in a separate space by using a polymer membrane during 1 to 10 passages; and subsequently transferred onto the feeder cells and cultured through a general procedure. When cultured through the general procedure after sub-cultured by using the polymer membrane, stem cells express Nanog RNA transcripts as an undifferentiation marker more highly than control groups does. In addition, they remain their characteristic of undifferentiation including colony shape.

Figure 2:
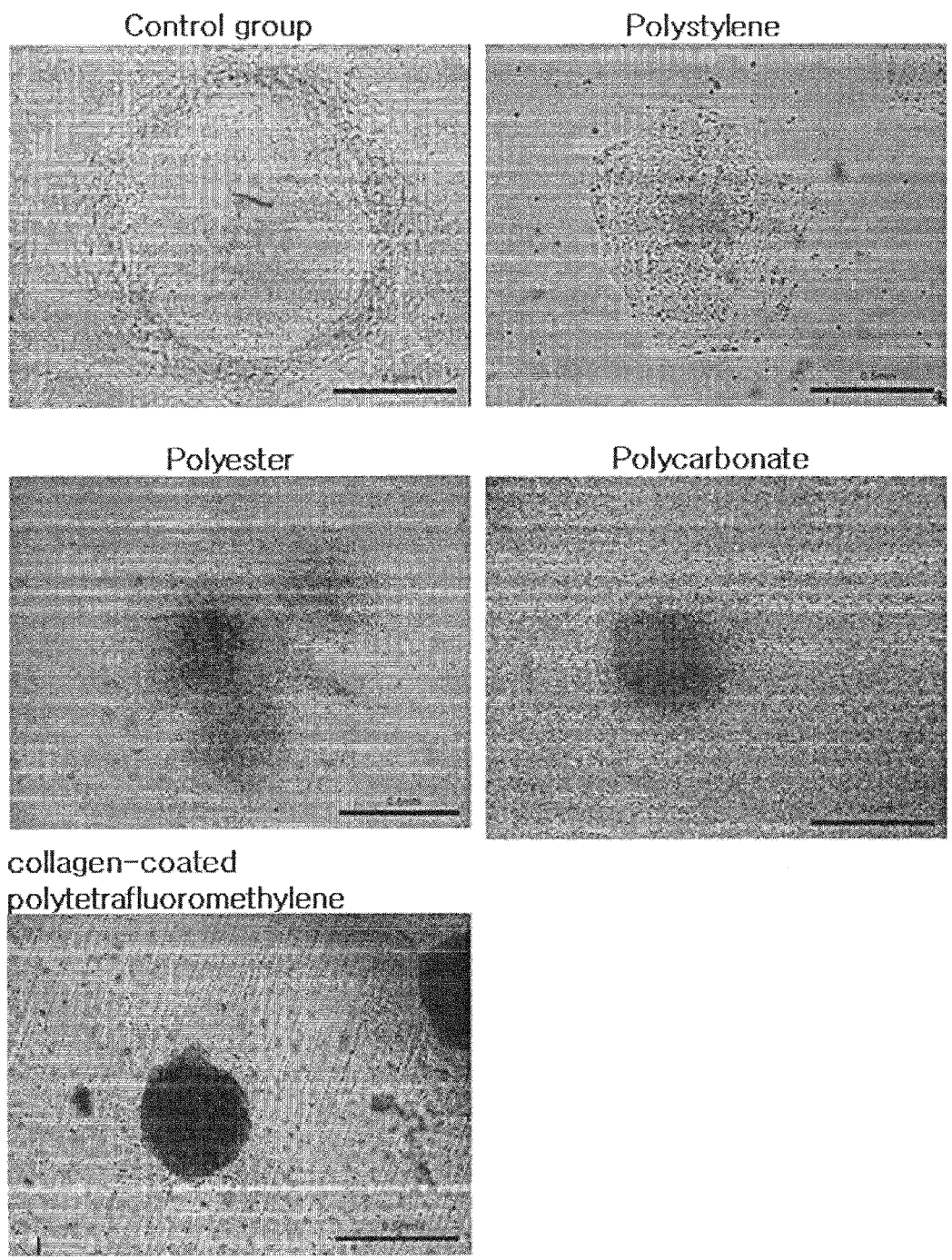
FIG. 2 depicts the colonies of embryonic stem cell HAF6 (72 passages; cultured for 5 days) according to culture conditions observed by a phase contrast microscope (40× magnification; scale bar 0.5 mm).
Figure 8:
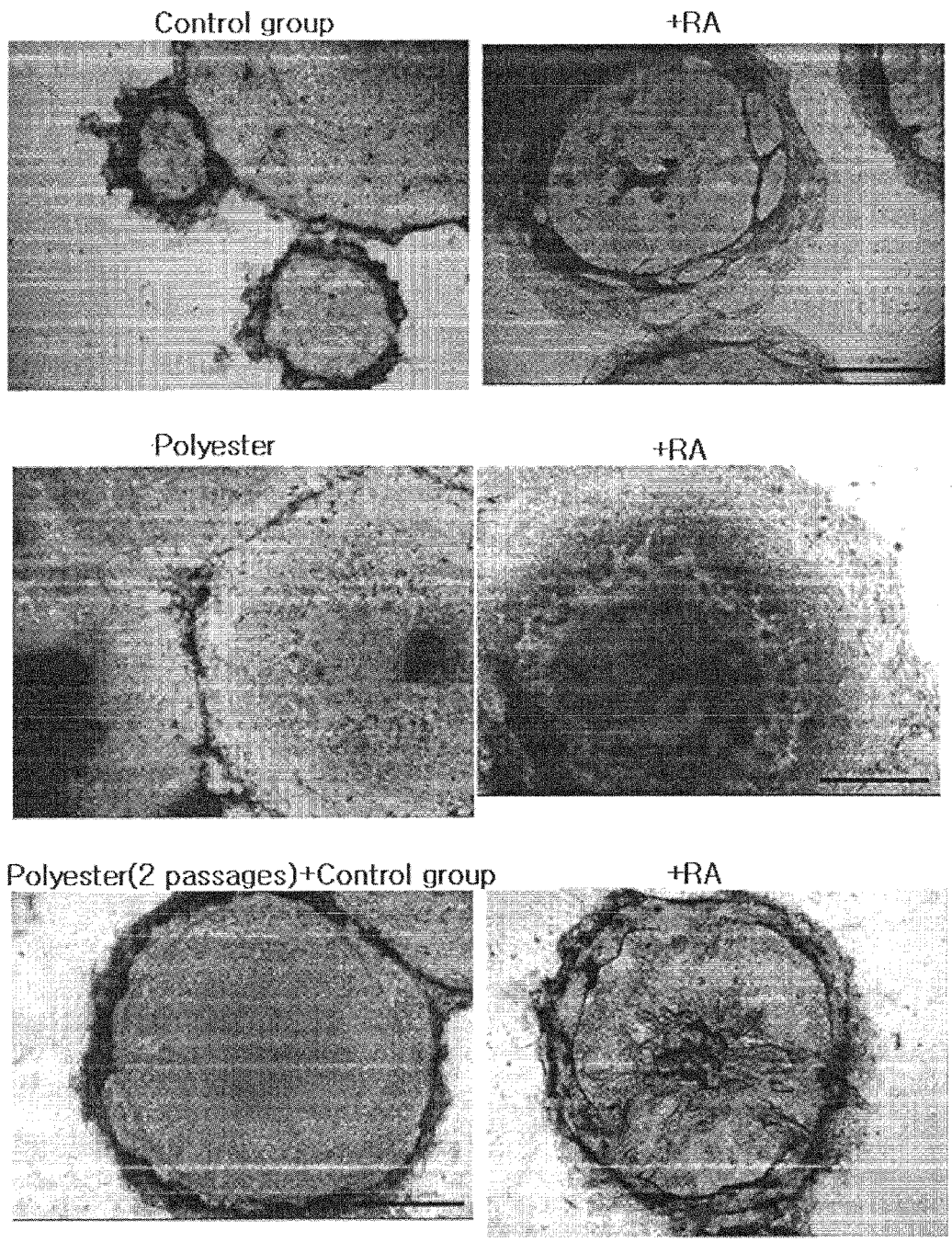
FIG. 8 depicts the embryonic stem cell HAF6 (72 passages; cultured for 5 days) treated with retinoic acid according to culture conditions by using an alkaline phosphatase staining (40× magnification; scale bar 0.5 mm).
Figure 17:
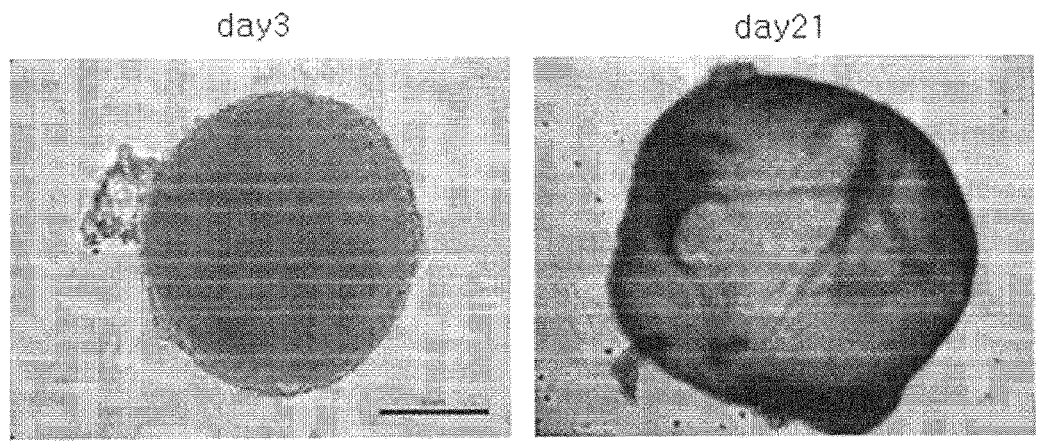
FIG. 17 depicts the formation of embryoid body (EB) measuring a tridermic differentiation.
Figure 18:
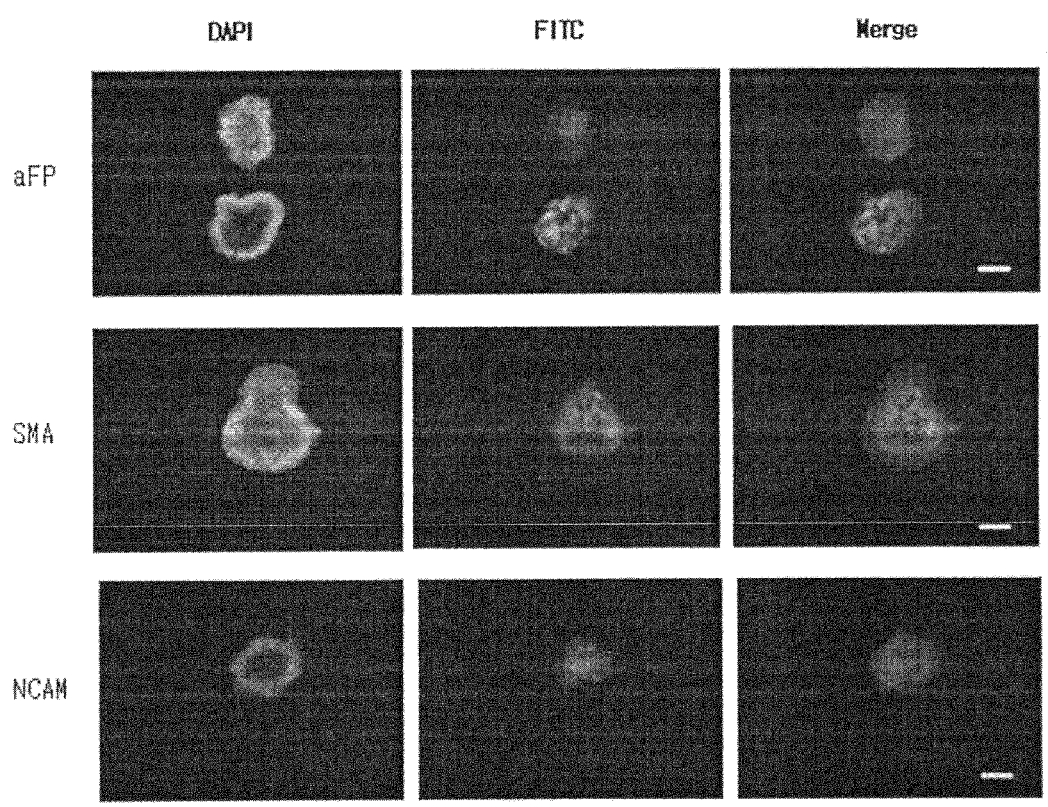
FIG. 18 depicts α-fetoprotein (aFP), an endodermic marker; smooth muscle actin (SMA), a mesodermic marker; and NCAM, an ectodermic marker that measures a tridermic differentiation by using a fluorescence staining.

In order to identify whether stem cells remain indifferent or not, human embryonic stem cells are observed by a phase contrast microscope (FIG. 2). Respectively, the stem cells are cultured through a conventional procedure or co-cultured by a novel procedure. Besides, human embryonic stem cells are monitored by using an alkaline phosphatase staining (FIG. 3); monitored in SSEA4 marker by using a fluorescence staining (FIG. 9); in Tral-60 marker by using a fluorescence staining (FIG. 10); and analyzed in Tral-60 marker by performing a FACS analysis (FIG. 11 to FIG. 13); in Nanog RNA transcripts by performing a real time PCR (FIG. 4); in tridermic markers by performing a PCR (FIG. 5); and compared in the total amount of genomic DNAs to measure a cell growth (FIG. 6); in the number of stem cells (FIG. 14); examined in chromosomal aberrations by performing a cytogenetic analysis (FIG. 15); in CD30 marker to detect a cell transformation by performing a FACS analysis (FIG. 16); in stem cells treated with retinoic acid by using a alkaline phosphatase staining to identify a cell differention (FIG. 8); in the formation of embryoid body (EB) (FIG. 17); in tridermic markers by using a fluorescence staining (FIG. 18). Human embryonic stem cells are analyzed in Nanog RNA transcripts by performing a real time PCR, when cultured through a conventional procedure after co-cultured by a novel procedure (FIG. 8). For co-culture use, 3 kinds of membranes such as polyester, polycarbonate, polytetrafluoroethylene are selected.

EXAMPLES

Practical and presently preferred embodiments of the present invention are illustrated as shown in the following Examples.

However, it will be appreciated that those skilled in the art, on consideration of this disclosure, may make modifications and improvements within the spirit and scope of the present invention.

Example 1

Cultivation of Embryonic Stem Cells in Control Group

Mouse embryonic fibroblasts were extracted from 13.5 day-pregnant mice (CFI, C57BL6) and primarily cultured. The resulting cells were treated with 10 μg/ml of mitomycin (Mitomycin C, Sigma, Cat. No. M-4287) as a cytostatic agent for one and a half hours to be used for feeder cells. Then, the resultants were inoculated in $4 \times 10^4/cm^2$ of cell density and on the next day, embryonic stem cells (HSF6) were seeded. In the composition of culture media, 3.069 g/l sodium bicarbonate (Sigma, USA, Cat. No. S5761), 2 mM L-glutamine (Sigma, Cat. No. S8540), 1% penicillin (50 U/ml; Sigma, Cat. No. P4687)/streptomysin (50 ug/ml; Sigma, USA, Cat. No. S1277), 20% Knock-Out serum replacement (SR; Invitrogen BRL, Cat. No. 10828-028), 4 ng/ml Basic Fibroblasts Growth Factor (bFGF; Invitrogen BRL, Cat. No. 13256-029) were added to basic DMEM/F12 medium (GIBCO, USA, Cat. No. 12500-062). The stem cells were cultivated at 37° C. in 5% $CO_2$ incubator while changing culture media every day.

Example 2

Co-Culture of Embryonic Stem Cells Using Semi-Permeable Membrane

Co-culture was performed by using general polystylene plates and commercially available transwells purchased from Corning Co. Ltd. Above all, mouse embryonic fibroblasts were treated with 10 μg/ml of mitomycin (Mitomycin C, Sigma, Cat. No. M-4287) as a cytostatic agent for one and a half hours to be used for feeder cells. Otherwise without mitomycin, the fibroblasts were inoculated in $5 \times 10^3/cm^2$ of cell density. Then on the next day, fresh culture media for embryonic stem cells was poured on the upper space and equilibriated. After monitoring equilibrium between upper and lower media, embryonic stem cells (HSF6) were seeded onto a membrane. In the composition of culture media, DMEM media (GIBCO, USA, Cat. No.) was blended with 3.7 g/l sodium bicarbonate (Sigma, USA, Cat. No. S5761), 2 mM L-glutamine (Sigma, Cat. No. S8540), penicillin (50 U/ml; Sigma, Cat. No. P4687)/streptomycin (50 ug/ml; Sigma, USA, Cat. No. S1277), 10% Fetal Bovine Serum (FBS; Hyclone, Cat. No. SH30070.03) and poured on 24-well plates respectively in 1.5 ml. Then on the polymer membrane inserted to 24 wells, DMEM/F12 media (GIBCO, USA, Cat. No. 12500-062) was mixed with 2.44 g/l sodium bicarbonate (Sigma, USA, Cat. No. S5761), 2 mM L-glutamine (Sigma, Cat. No. S8540), penicillin (50 U/ml; Sigma, Cat. No. P4687)/streptomycin (50 ug/ml; Sigma, USA, Cat. No.

Figure 1B:
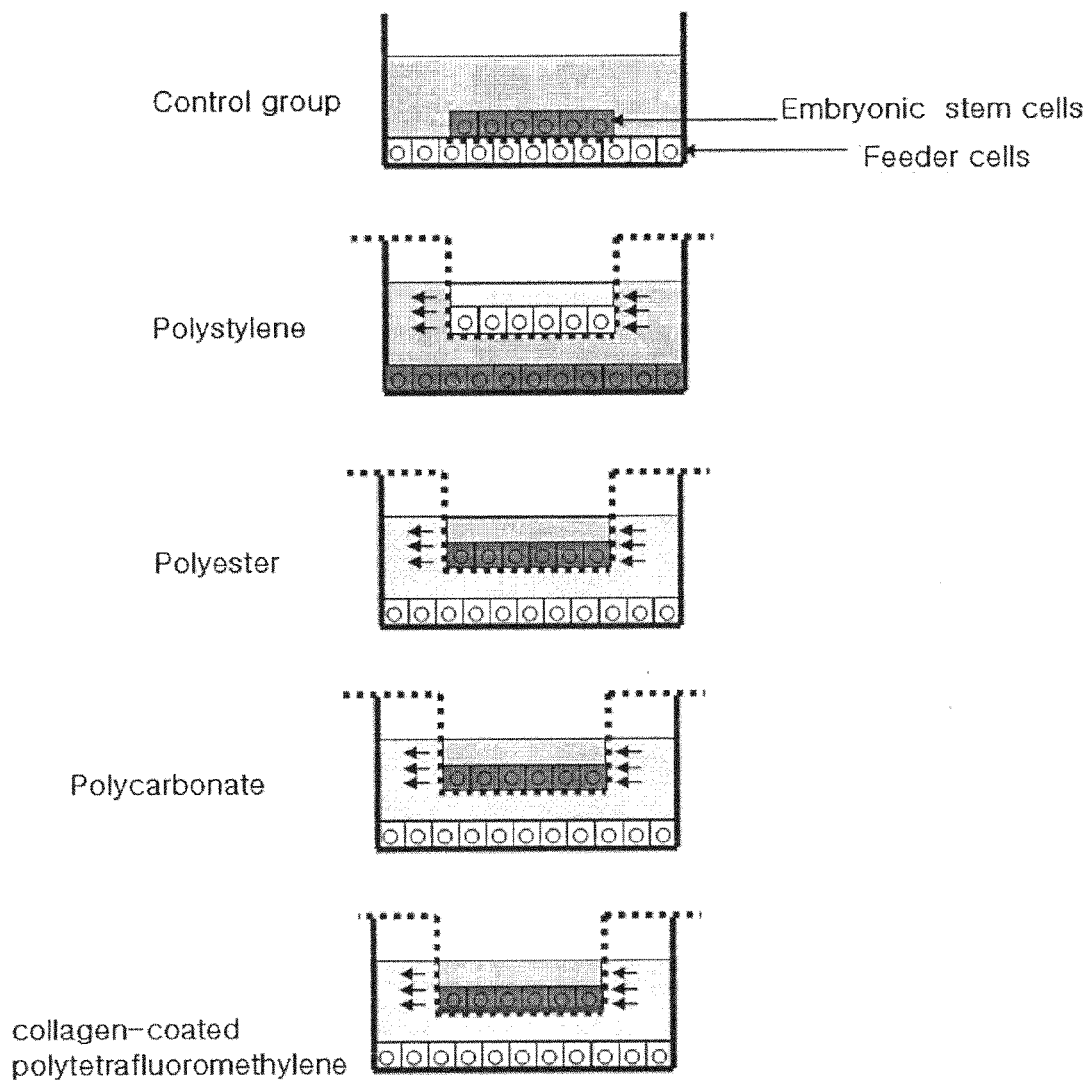
FIG. 1b is representative examples of FIG. 1a according to the kind of a semi-permeable membrane (polystylene, polyester, polycarbonate or collagen-coated polytetrafluoroethylene).

S1277), 20% Knock-Out serum replacement (SR; Invitrogen BRL, Cat. No. 10828-028), 4 ng/ml Basic Fibroblasts Growth Factor (bFGF; Invitrogen BRL, Cat. No. 13256-029) and added respectively in 0.5 ml for embryonic stem cell use. According to cases, the positions that inoculate feeder cells and embryonic stem cells were interchanged. Culture media was freshly changed every day. FIG. 1 is a schematic diagram of co-culture of stem cells using semi-permeable membrane. "Control group" depicts simple co-culture of feeder cells and embryonic stem cells. "Polystyrene" illustrates co-culture in which embryonic stem cells are spread on a polystyrene plate and feeder cells are laid on a semi-permeable polyester membrane. "Polyester" illustrates co-culture in which feeder cells are spread on a polystyrene plate and embryonic stem cells are laid on a semi-permeable polyester membrane. "Polycarbonate" illustrates co-culture in which feeder cells are spread on a polystyrene plate and embryonic stem cells are laid on a semi-permeable polycarbonate membrane. "Collagen-coated polytetrafluoroethylene" illustrates co-culture in which feeder cells are spread on a polystyrene plate and embryonic stem cells are laid on a semi-permeable polytetrafluoroethylene membrane coated with collagen.

Example 3

Alkaline Phosphatase Staining

Human embryonic stem cells were selected by using alkaline phosphatase staining. Stained colonies of stem cells were judged to remain indifferent and counted. Clear colonies without staining were judged to be differentiated and calculated. In order to perform alkaline phosphatase staining, NBT/BCIP (Roche, Germany, Cat. No. 1 681 451) solution was added to Tris-Cl (pH 9.5) buffer in 99:1 of ratio and reacted. Then, coloring reaction was monitored (See FIGS. 3 and 8; Experimental results 1 and 2).

Example 4

Fluorescence Staining of SSEA4

Figure 9:
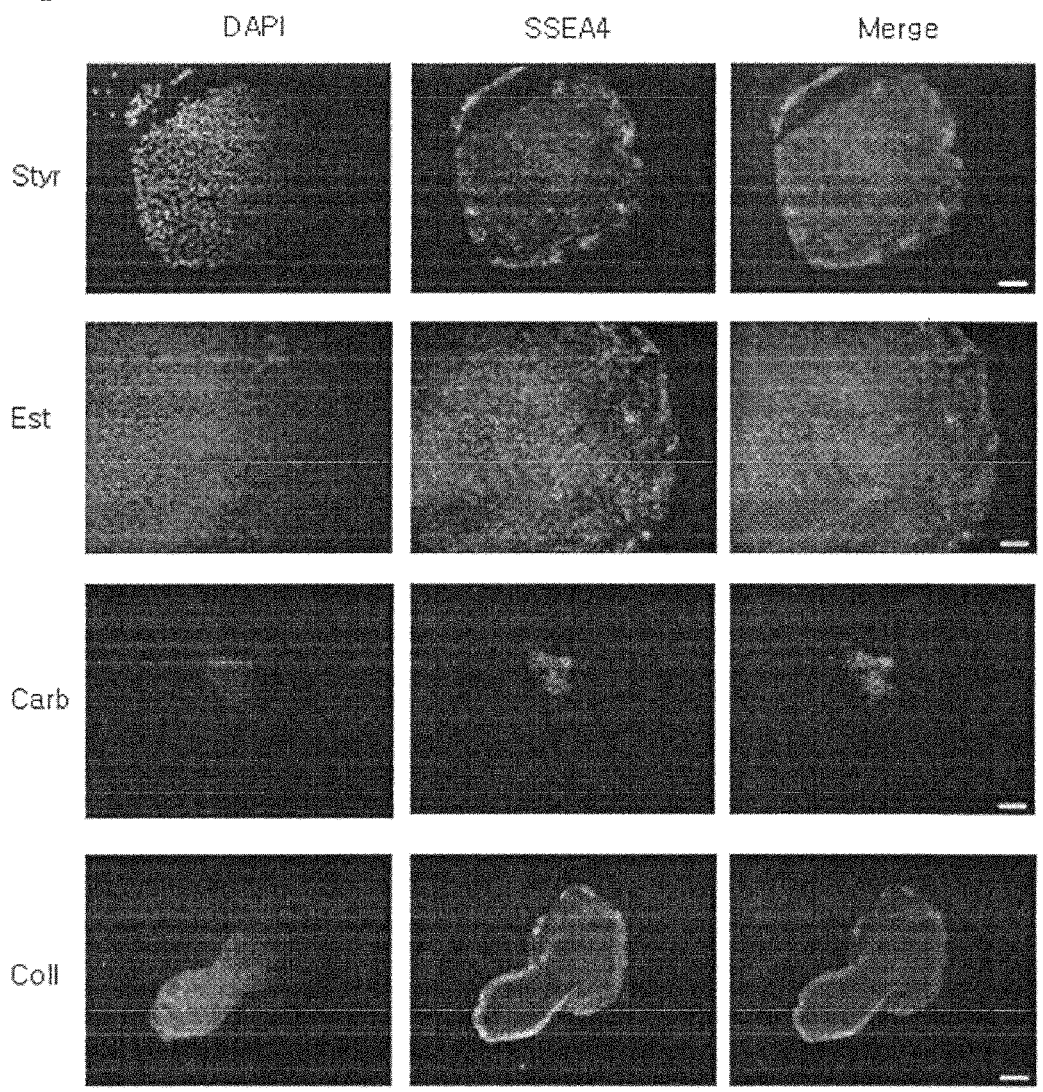
FIG. 9 depicts SSEA4, an undifferentiation marker magnified in 100-fold (10× magnification; scale bar: 10 μm) by using a fluorescence staining.

Embryonic stem cells were fixed by using para-formaldehyde and treated with 0.1% of Triton-X100 to become permeable. Then, the resulting cells were reacted with stage-specific embryonic antigen 4 (SSEA4, Chemicon, USA) as a primary antibody at 4° C. for more than 3 hours and washed off by using phosphate buffered saline (PBS) containing 1% of bovine serum albumin (BSA). After that, the resultants were reacted FITC-conjugated anti-mouse antibody (Jackson ImmunoResearch, USA) as a secondary antibody for about 1 hour. Then, DAPI was treated for about 5 minutes to stain nuclei. FIG. 9 depicts fluorescent staining data of undifferentiation marker SSEA4 and magnified in 100-fold (scale bar: 10 μm). This data may inform whether stem cells remain indifferent onto a polymer membrane or not. As a result, it is identified that the stem cells seeded on a polyester membrane should more express SSEA4 marker than any stem cells on other membranes.

Example 5

Fluorescence Staining of Tra1-60

Figure 10:
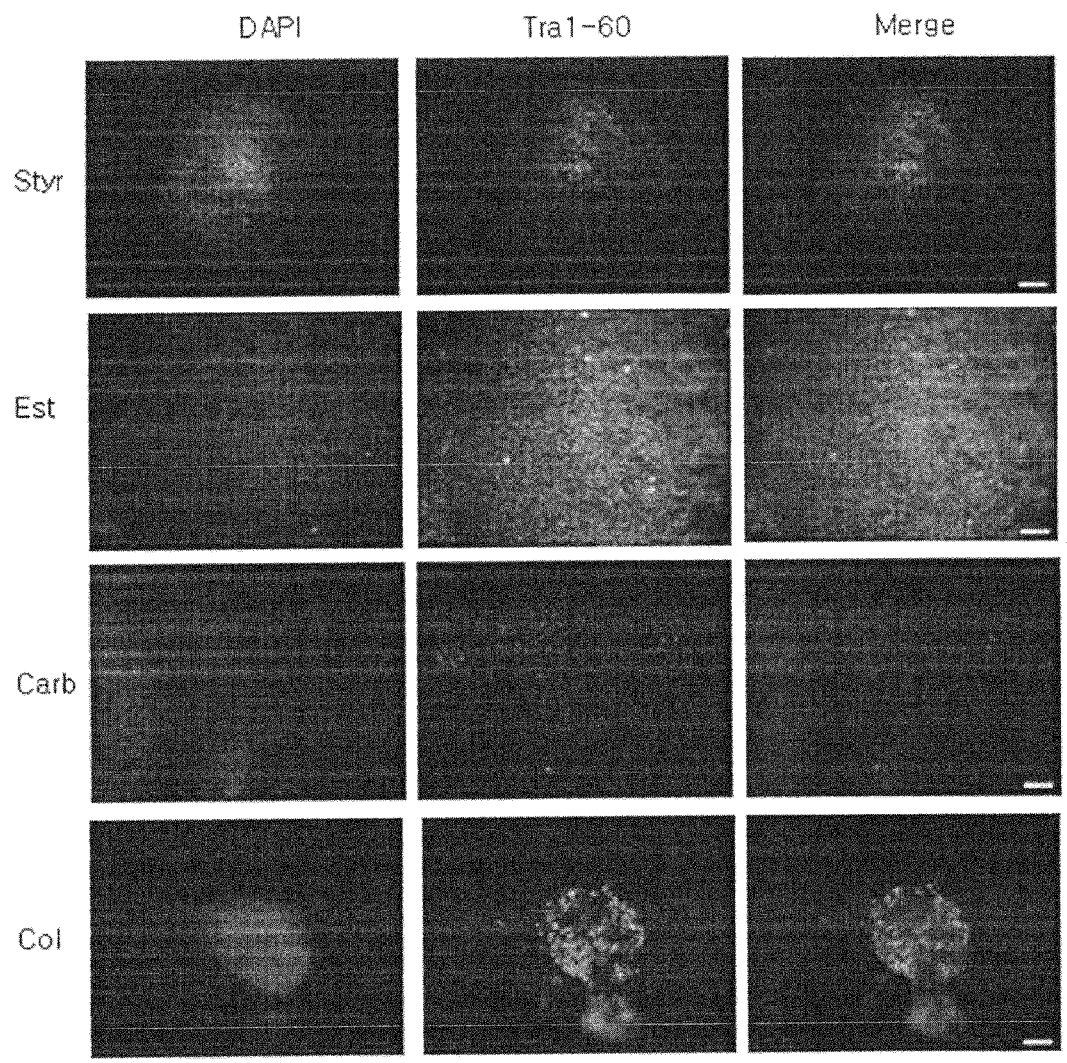
FIG. 10 depicts Tra1-60, another undifferentiation marker magnified in 100-fold (10× magnification; scale bar: 10 μm) by using a fluorescence staining.

Tumor-rejection antigen-60 (Tra1-60, Chemicon, USA) was fluorescence-stained by using Tra1-60 as a primary antibody and FITC-conjugated anti-mouse antibody as a secondary antibody. The same procedure is accomplished as described in Example 4. FIG. 10 depicts fluorescent staining data of another undifferentiation marker Tral-60 and magnified in 100-fold (scale bar: 10 μm). This data may inform whether embryonic stem cells should remain indifferent or not. As a consequence, it is also identified that the stem cells seeded on a polyester membrane should express Tral-60 marker most stably.

Example 6

Flow Cytometry of Tral-60

Figure 11:
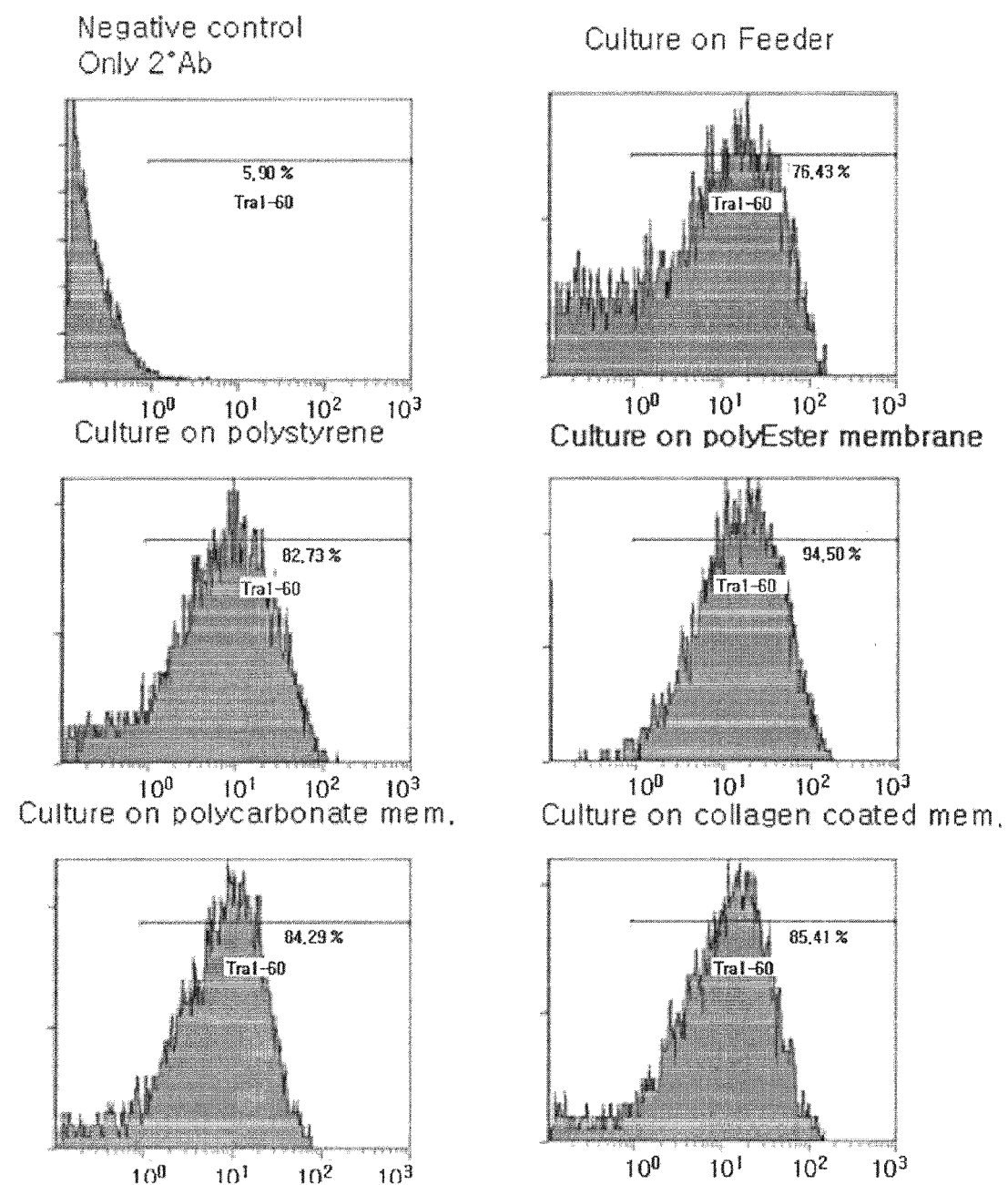
FIG. 11 depicts the surface expressions of Tra1-60 an undifferentiation marker according to culture conditions by performing a FACS analysis.
Figure 12:
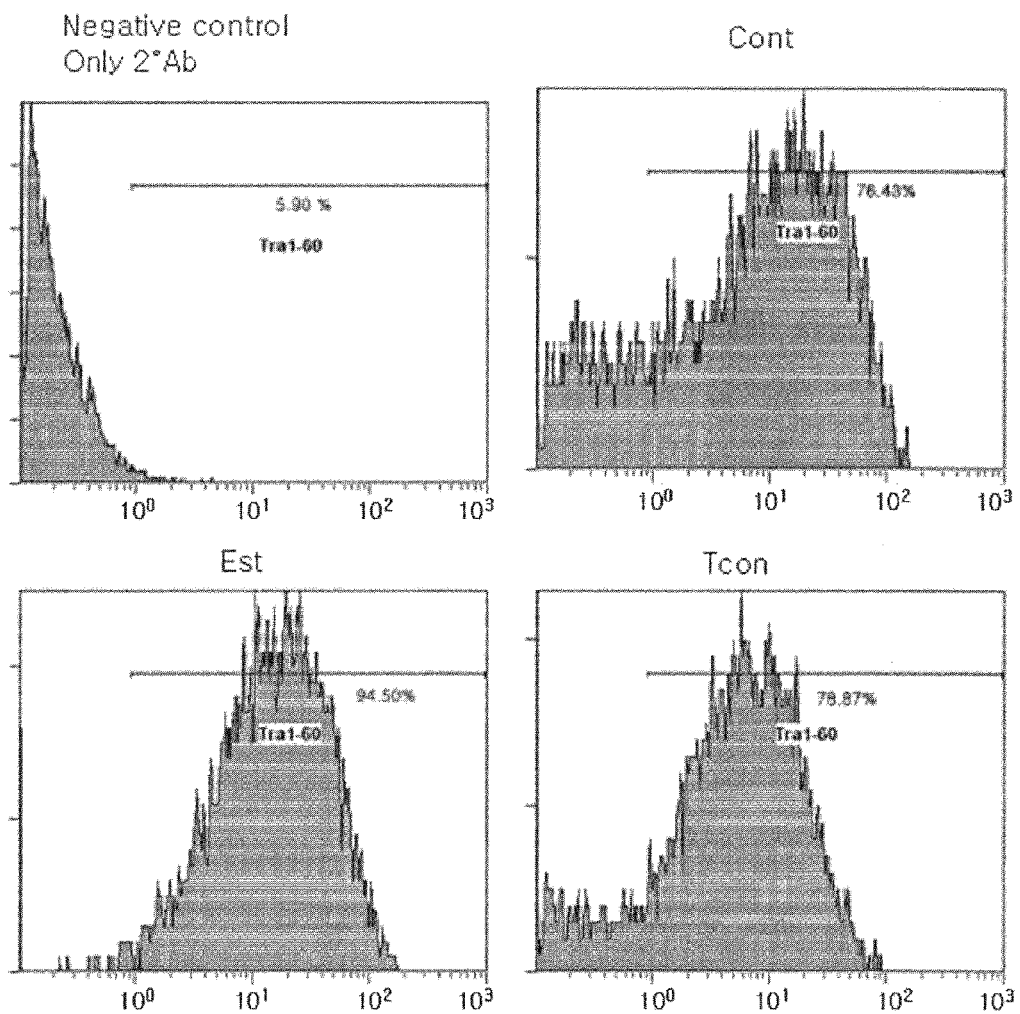
FIG. 12 depicts the variation of the surface expression of Tra1-60 by performing a FACS analysis.
Figure 13:
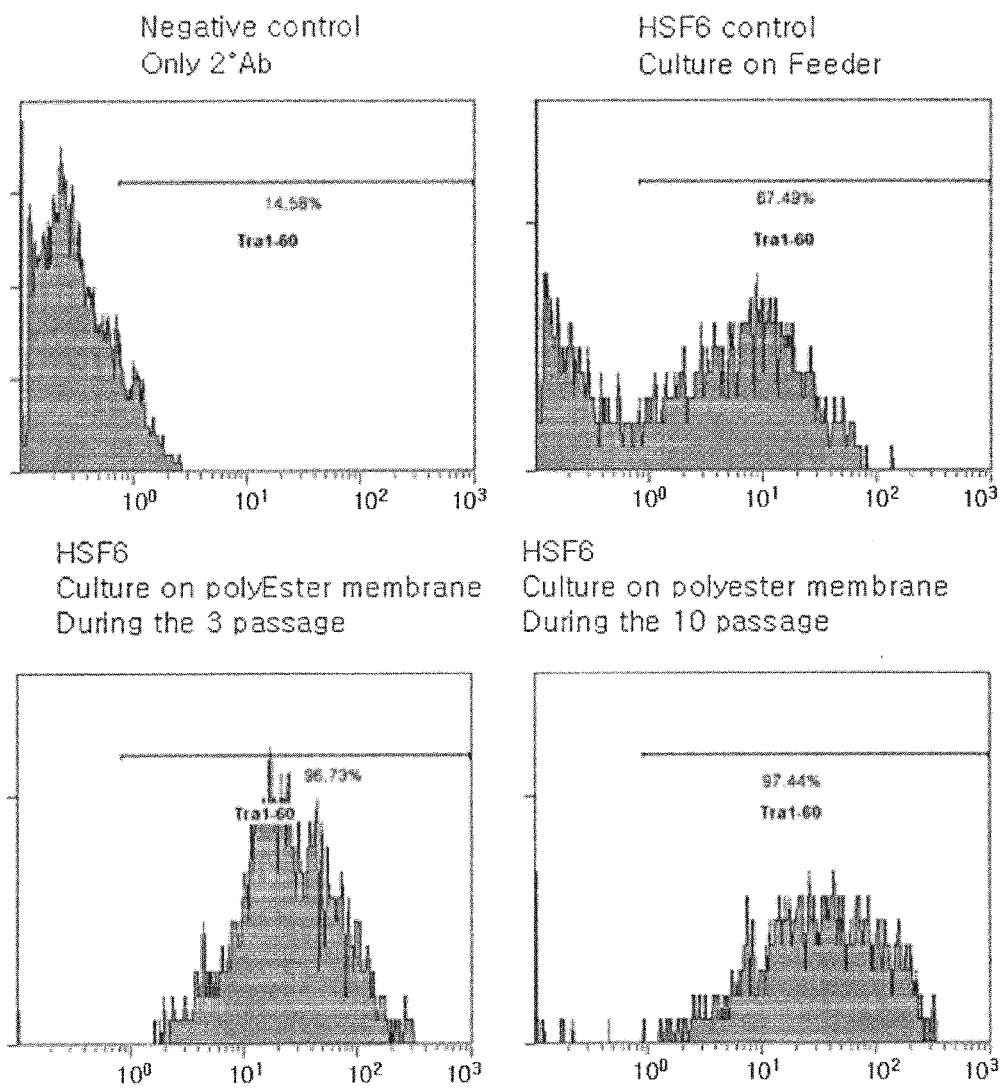
FIG. 13 depicts the variation of the surface expressions of Tra1-60 during a long-term culture by performing a FACS analysis.

Embryonic stem cells were suspended to mono-cells and reacted with Tral-60 as a primary antibody at a low temperature for more than 3 hours. Then, the resulting cells were treated for about 1 hour with secondary antibodies and fixed with para-formaldehyde. The resultant was analyzed by performing flow cytometry (FACS). FIG. 11 depicts the cell surface expression of Tral-60 marker by performing FACS analysis. This result may inform how much embryonic stem cells remain indifferent under various culture conditions. Table 1 illustrates Tral-60 cell surface expression (%) measured in FIG. 11. As a consequence, it is observed that the undifferentiation marker of a polyester membrane case is most highly expressed on the cell surface. Therefore, it is confirmed that the cell culture on the polyester membrane is most suitable not to induce differentiation. In the control group seeded on feeder cells, the surface expression of Tral-60 marker is observed very low because differentiated cells may be mingled or inactive feeder cells may be inserted. FIG. 12 depicts the variation of the cell surface expressions of Tral-60 by performing a FACS analysis. This result may inform how the surface expression of undifferentiation markers varied, when embryonic stem cells cultured on a polyester membrane are transferred onto feeder cells. As a consequence, it is identified that embryonic stem cells cultured on a polyester membrane should reveal a high expression, but increase cell portion without the label when transferred onto feeder cells after more than 3 passages. It is deduced that feeder cells are mixed while collecting cells. FIG. 13 depicts the variation of the surface expressions of Tral-60 during a long-term culture by performing a FACS analysis. This result may inform that embryonic stem cells could remain indifferent when cultured on a polyester membrane for a long period. As a result, it is confirmed that embryonic stem cells could express an undifferentiation marker normally even though on a polyester membrane during a long-term culture.

TABLE 1

| Material | Tra1-60 cell surface expression (%) |
|---|---|
| Negative control Only 2° Ab | 5.90% |
| Culture on Feeder | 76.43% |
| Culture on polystyrene | 82.73% |
| Culture on polyEster membrane | 94.50% |
| Culture on polycarbonate membrane | 78.87% |
| Culture on collagen coated membrane | 84.29% |

Example 7

Reverse Transcription Polymerase Chain Reaction and Real-Time Reverse Transcription Polymerase Chain Reaction Human embryonic stem cells were collected from each experimental group and washed by using phosphate buffered saline. The stem cells were centrifuged at 3,000 rpm for 5 minutes to discard supernatant. The cell pellet was treated with Trizol (Invitrogen, Rockville, Cat. No. 15596-018) to isolate RNA. In order to reverse transcription polymerase chain reaction (RT-PCR), about 500 ng of RNA and random hexamer as a primer were utilized so as to prepare cDNAs by using reverse transcriptase AMV (Roche, Germany, Cat. No. 10 109 118 001). Then, 100-200 ng of the resulting cDNAs was allotted with sense primer, anti-sense primer (for b-actin, a-FP, KDR, NCAM) and PCR premix (PerMix, BioNEER, Korea, Cat. No. K-2016) and reacted with distilled water. PCR was conducted to 20 to 30 cycles under a following condition: 94° C. 45 sec; 60° C. 45 sec and 72° C. 45 sec. 5 µl of the PCR product was analyzed by performing a 1% agarose gel electrophoresis (See FIG. 5; Experimental Result 1)

In order to real-time reverse transcription polymerase chain reaction (RT-PCR), RNAs were prepared to obtain cDNA by performing the same procedure of RT-PCR described above. 100 to 200 ng cDNA, sense primer and anti-sense primer (for Nanog) and fluorescent PCR premix (iQ™ SYBR® Green Supermix, BIO-RAD, Calif.) were reacted with distilled water. Real-time PCR was conducted to 30 to 40 cycles with BIO-RAD real-time PCR machine to analyze its result.

Example 8

Extraction Genomic DNA and Measurement of Quantity

Human embryonic stem cells were collected from each experimental group and washed off by using phosphate buffered saline. The resulting cells were centrifuged at 3,000 rpm for 5 minutes to discard supernatant. The cell pellet was treated with Trizol (Invitrogen, Rockville, Cat. No. 15596-018) to isolate genomic DNAs. Then, the resulting DNA was analyzed by measuring its absorbance (See FIG. 6; Experimental Result 2)

Example 9

Measurement of Cell Number

Figure 14:
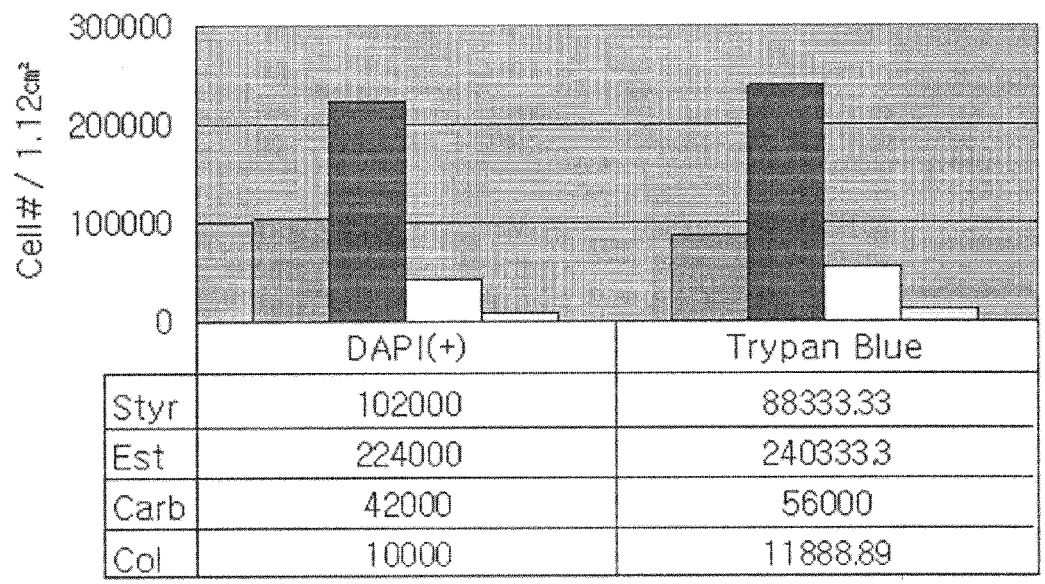
FIG. 14 depicts the number of cells calculated by using a DAPI staining and a trypan blue staining.

Human embryonic stem cells were suspended to monocells and reacted with DAPI for 3 minutes. Then, cell nuclei were stained and calculated under a fluorescence microscope to obtain the number of cells. Otherwise, the stem cells may be stained with trypan blue to measure the number. FIG. 14 depicts the numbers of cells calculated by using a DAPI staining and a trypan blue staining. In order to observe the degrees of cell growth, the numbers of cells were calculated under a fluorescence microscope. Table 2 illustrates the number of cells (cell #/1.12 cm$^2$) measured in FIG. 14. As a consequence, it is identified that in both cases of DAPI staining and trypan blue staining, the stem cells should proliferate most actively while using a polyester membrane. This result accords with that of genomic DNAs described above.

TABLE 2

| | Cell#/1.12 cm$^2$ | | | |
| --- | --- | --- | --- | --- |
| | | Trypan Blue | | |
| Material | DAPI(+) | 1st | 2nd | Average |
| Styr | 102000 | 90000 | 86666.7 | 88333.33 |
| Est | 224000 | 264000 | 216666.7 | 240333.3 |
| Carb | 42000 | 52000 | 60000 | 56000 |
| Col | 10000 | 6000 | 17777.8 | 11888.89 |

Example 10

Cytogenetic Analysis

Figure 15:
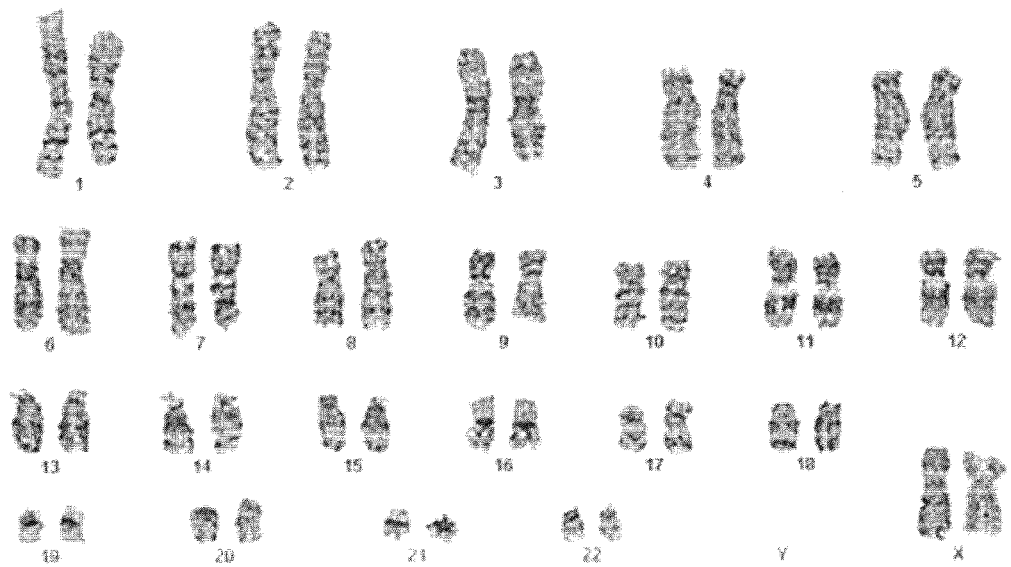
FIG. 15 depicts the karyotypings (at least 25 cases) of embryonic stem cells cultured on a polymer membrane that monitors chromosomal aberrations.

In order to observe chromosomal aberrations, cell karyotypes were analyzed. Above all, embryonic stem cells were sub-cultured to more than 4-passages onto a polyester membrane to become confluent. The resulting cells were treated with colcemide (0.1 µg/ml; Invitrogen) and suspended to mono-cells. After fixing the cells, G-band was observed on a glass slide. FIG. 15 depicts the karyotype data of embryonic stem cells. The embryonic stem cells cultured on a polymer membrane were analyzed by performing a karyotyping to monitor chromosomal aberrations. This karyotyping has been attempted in at least 25 cases. As a result, it is identified that embryonic stem cells does not reveal a chromosomal aberration even if sub-cultured to more than 4-passages onto a polyester membrane.

Example 11

Flow Cytometry of CD30

Figure 16:
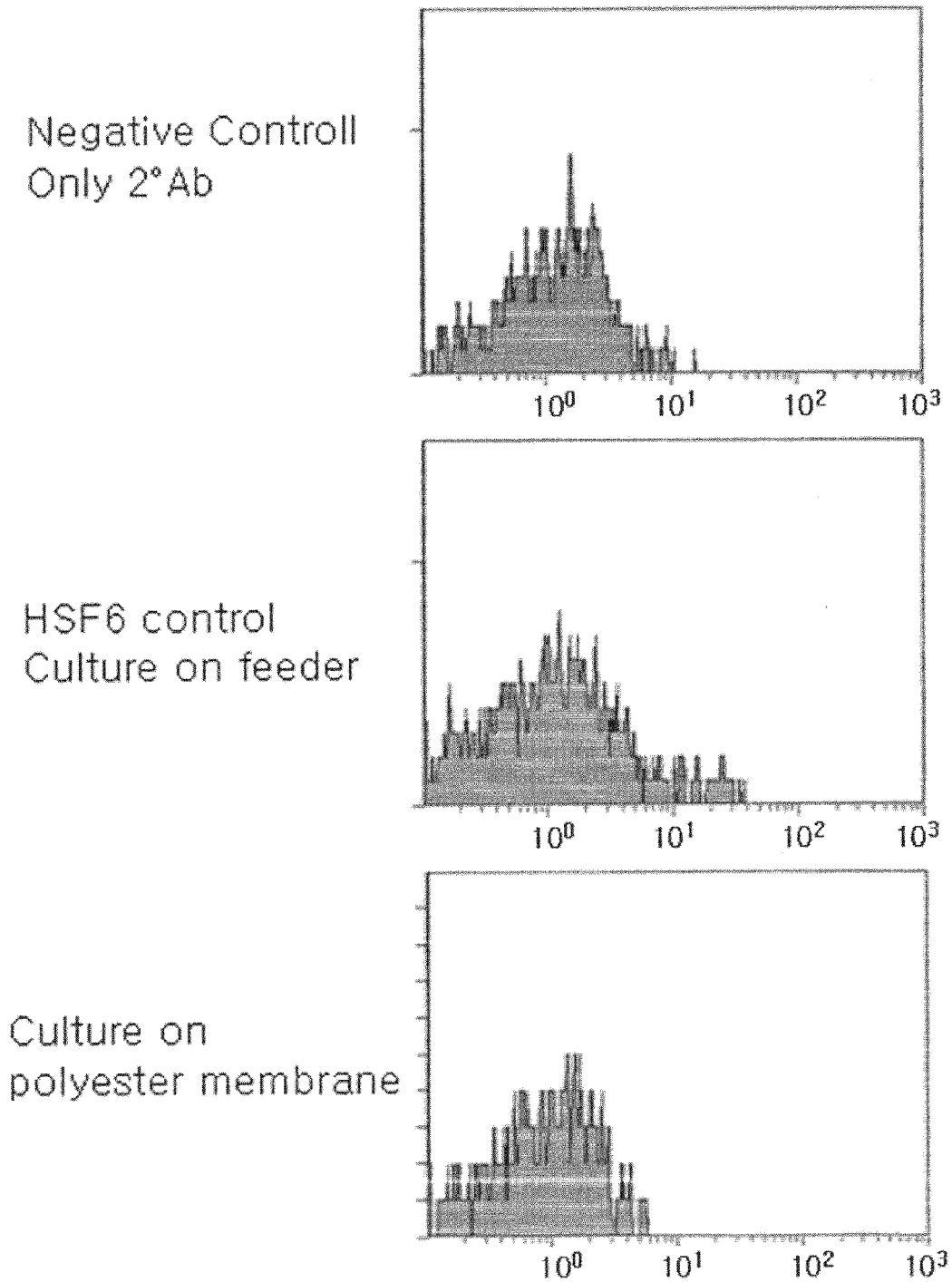
FIG. 16 depicts CD30, a transformation marker detected by performing a FACS analysis.

Presently, CD30 is most common marker that reveals the transformation of embryonic stem cells. Embryonic stem cells were suspended to mono-cells and reacted with a primary antibody CD30 at a low temperature for more than 3 hours. Then, the resulting cells were treated with a secondary antibody for about 1 hour and fixed by using para-formaldehyde. The surface expression of CD30 was analyzed by performing FACS. FIG. 16 depicts CD30 marker as a cell transformation marker detected by performing a FACS analysis. In order to observe whether stem cells are transformed on a polymer membrane, CD30 marker was traced. As a consequence, it is observed that the embryonic stem cells cultured on a polyester membrane should be normal cells that does not express CD30 marker as those of the control group.

Example 12

Induction of Differentiation Using Retinoic Acid

Human embryonic stem cells were induced to differentiate at 2 days after inoculated. At this moment, the embryonic stem cells started to spread and form colonies. All-trans-retinoic acid was dissolved in DMSO solution and dropped into culture media to adjust $10^{-6}$ M of final concentration. Then, the retinoic acid solution continued to be treated every day for 3 days. Culture media was exchanged every day with fresh culture media for 4 days. The control group was not treated with any solution, while exchanging every day with fresh culture media for 5 days.

Example 13

Formation of Embryoid Body and Fluorescence Staining of Tridermic Marker

Colonies of embryonic stem cells were cut to proper pieces and cultured onto a hydrocell (Japan) that is specially coated not to coagulate cells. At this moment, DMEM/F12 media containing 10% Knockout serum replacement and 2% FBS was utilized and floated a membrane for colons to make embryoid bodies (EB). The resulting EBs were fixed by using para-formaldehyde and treated with Triton-X100 to absorb antibodies effectively. Then, the cells were reacted with a primary antibody at a low temperature for more than 3 hours and washed off. After that, they were reacted with a secondary antibody for an hour and stained with DAPI to dye cell nuclei. In order to identify the capacity of differentiation, the embryonic stem cell cultured on a polyester membrane was made to an embryoid body and fluorescence-stained by using endodermic, mesodermic and ectodermic markers. The resultant was observed under a fluorescence microscope to detect the expression of fluorescent markers. FIG. 17 depicts the formation of embryoid bodies. Embryonic stem cells were induced to form EBs and measured the capacity of differentiation. FIG. 18 depicts the fluorescence-stained markers showing α-fetoprotein (aFP) as an endodermic marker; smooth muscle actin (SMA) as a mesodermic marker; and NCAM as an ectodermic marker. Induced EBs were observed to measure the capacity of differentiation. As a consequence, it is confirmed that embryonic stem cells cultured according to the present invention could form embryoid bodies and differentiate toward endoderm, mesoderm and ectoderm.

Example 14

Examination of Characteristics of Cell Culture According to Porosity

Figure 19:
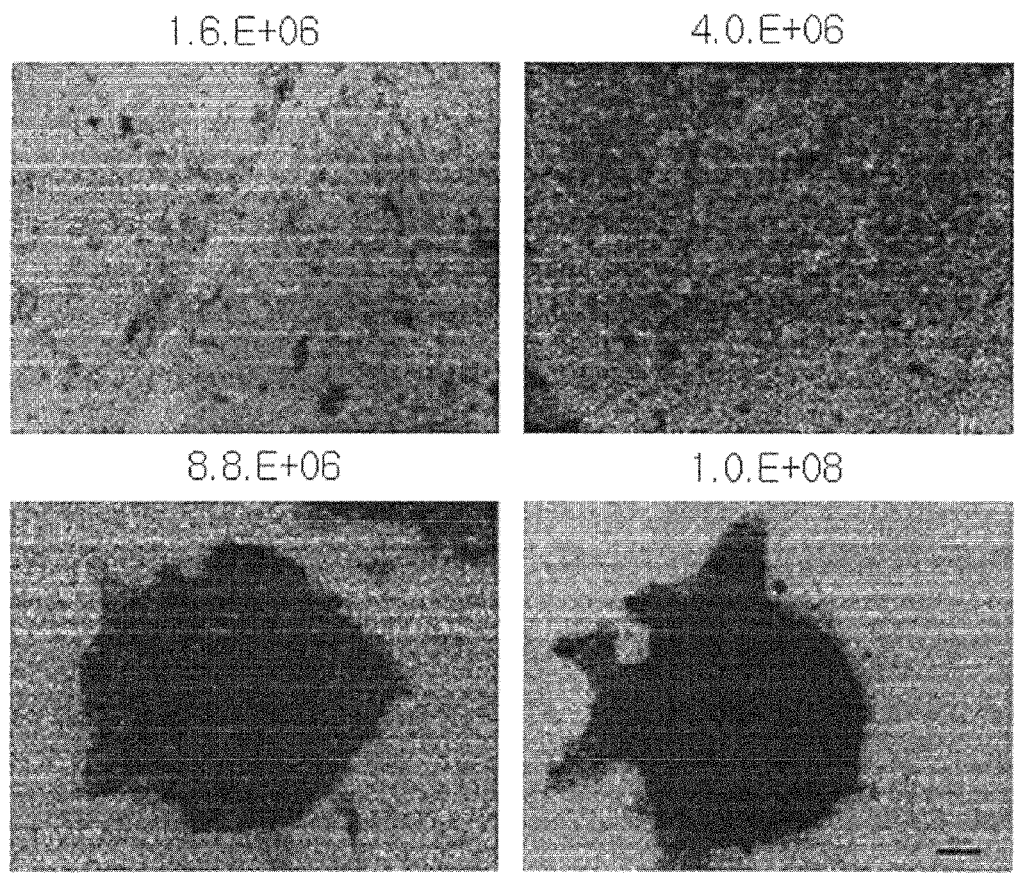
FIG. 19 depicts the degrees of undifferentiation of stem cells according to the pore density of a membrane by using an alkaline phosphatase staining.
Figure 20:
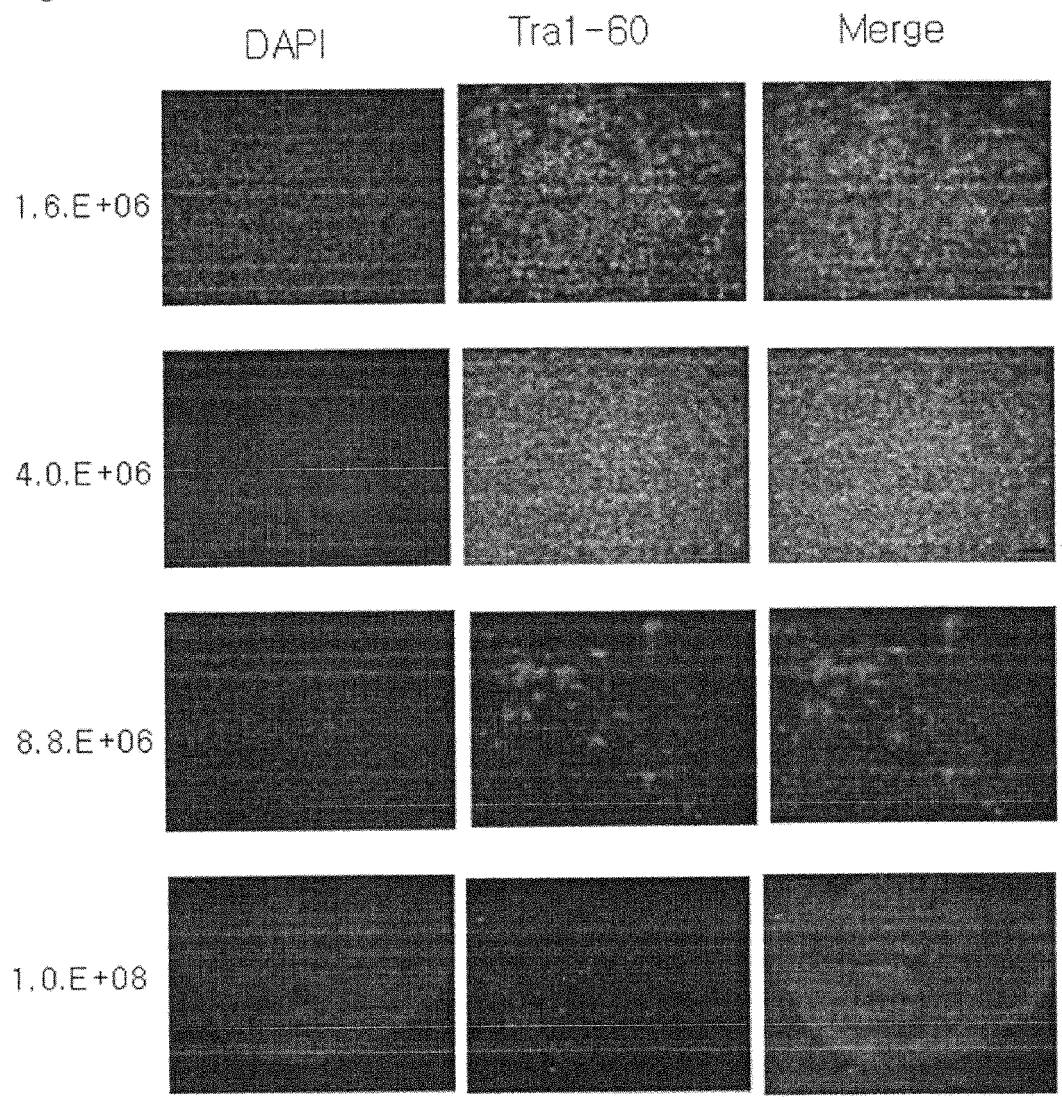
FIG. 20 depicts the degrees of undifferentiation of stem cells according to the pore density of a polyester membrane by using a fluorescence staining.
Figure 21:
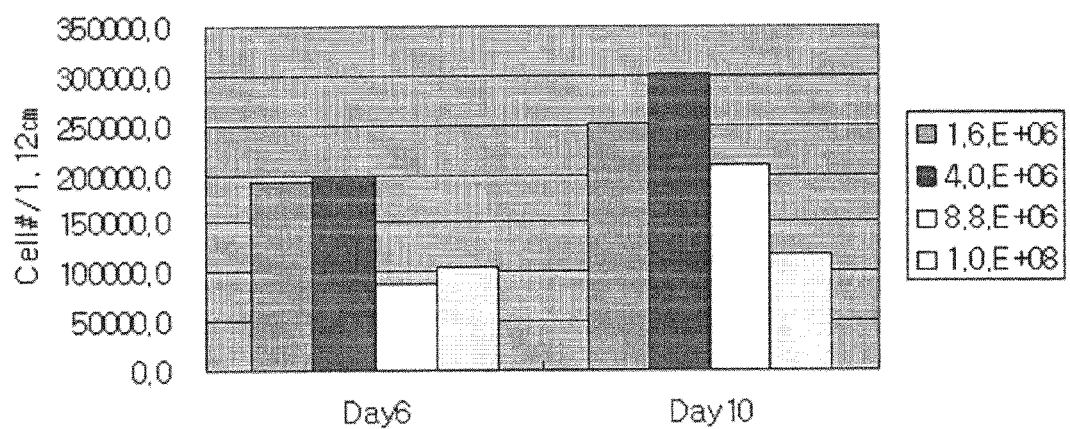
FIG. 21 depicts the cell growth according to the pore density of polyester membrane by using a trypan blue staining.

A number of polyester membranes different in the density (per unit $cm^2$) of pores were prepared to cultivate embryonic stem cells. In order to observe whether stem cells remain indifferent or not, alkaline phosphatase staining was conducted by the same procedure described above to dye undifferentiation markers. In order to measure the ratio of cell growth, the number of cells was counted after stained with trypan blue. FIG. 19 depicts the degrees of undifferentiation of stem cells according to the pore density of a membrane by staining with alkaline phosphatase. The markers (scale bar: 20 µm) detected whether stem cells could remain indifferent. When the porosity increased, embryonic stem cells cannot grow normally and tended to form embryoid bodies. In contrast, when the porosity decreased, embryonic stem cells tended to differentiate naturally. As a result, it is judged that the porosity could be adjusted in the range of 2.0.E+06 to 6.0.E+06. FIG. 20 depicts the fluorescence-stained Tral-60 markers that detects whether stem cells could remain indifferent according to the pore density of polyester membrane. When the porosity increased, embryonic stem cells decreased the capacity remaining indifferent. In contrast, when the porosity decreased, mono-cells within an embryonic stem cell clone tended to become larger. FIG. 21 depicts the cell growth according to the pore density of polyester membrane by using a trypan blue staining. In order to observe the cell growth, the numbers of cells were calculated directly. Table 3 illustrates the number of cells (cell #/1.12 $cm^2$) measured in FIG. 21. When the porosity became higher, the cell growth decreased.

TABLE 3

| | Cell#/1.12 $cm^2$ | |
|---|---|---|
| Pores/$cm^2$ | Day 6 | Day 10 |
| 1.6.E+06 | 192000.0 | 252000.0 |
| 4.0.E+06 | 198000.0 | 302000.0 |
| 8.8.E+06 | 88000.0 | 210000.0 |
| 1.0.E+06 | 106000.0 | 118000.0 |

Figure 3:
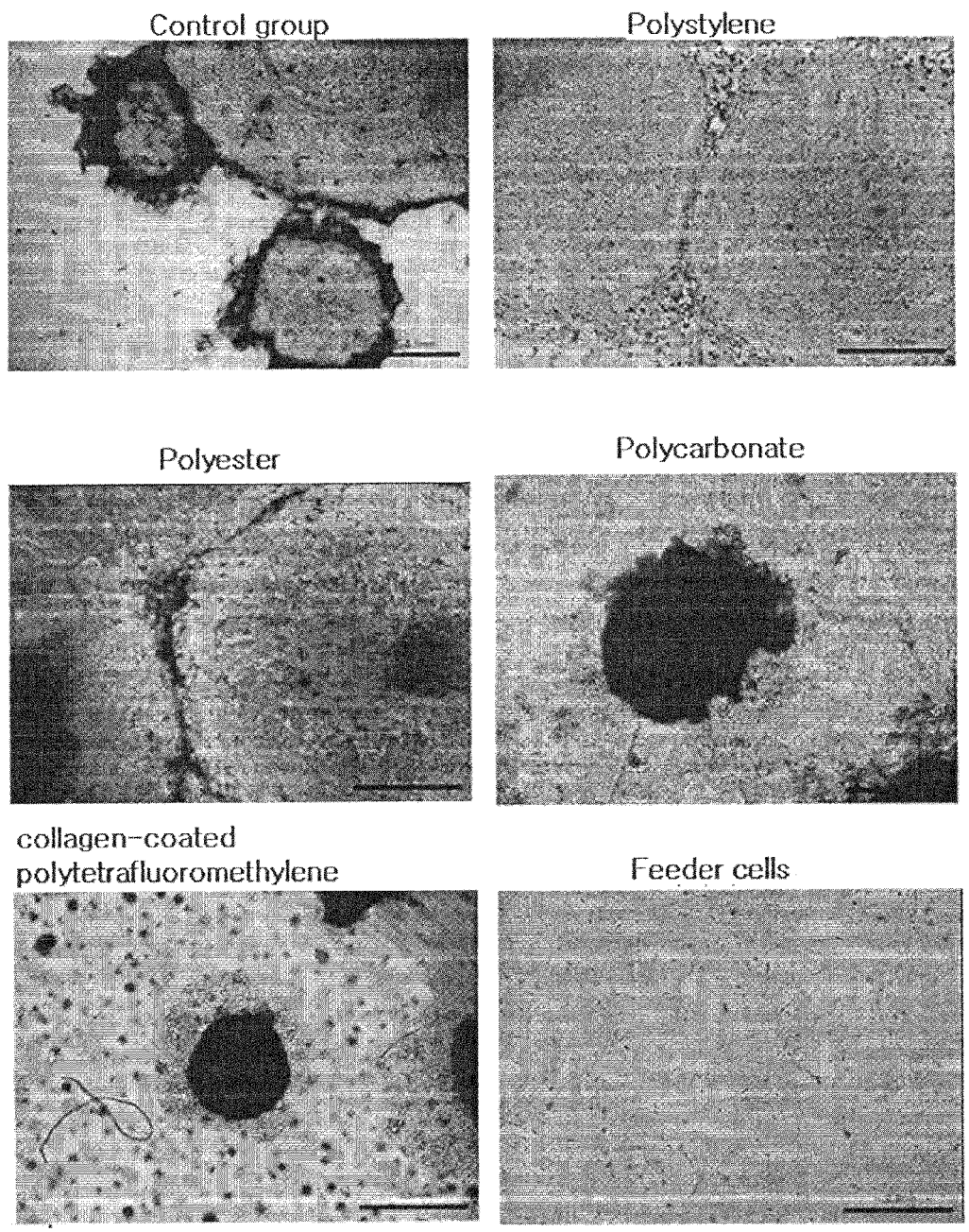
FIG. 3 depicts the degrees of undifferentiation of embryonic stem cell HAF6 (72 passages; cultured for 5 days) according to culture conditions by using an alkaline phosphatase staining (40× magnification; scale bar 0.5 mm).
Figure 4:
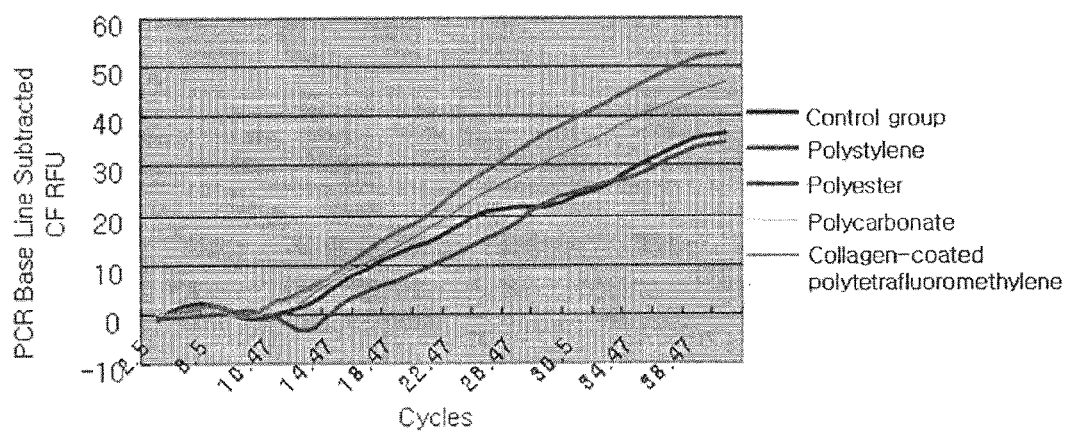
FIG. 4 depicts the expression of Nanog RNA transcripts, an undifferentiation marker of embryonic stem cell HAF6 (72 passages; cultured for 5 days) according to culture conditions by performing a real-time reverse transcription polymerase chain reaction.
Figure 6:
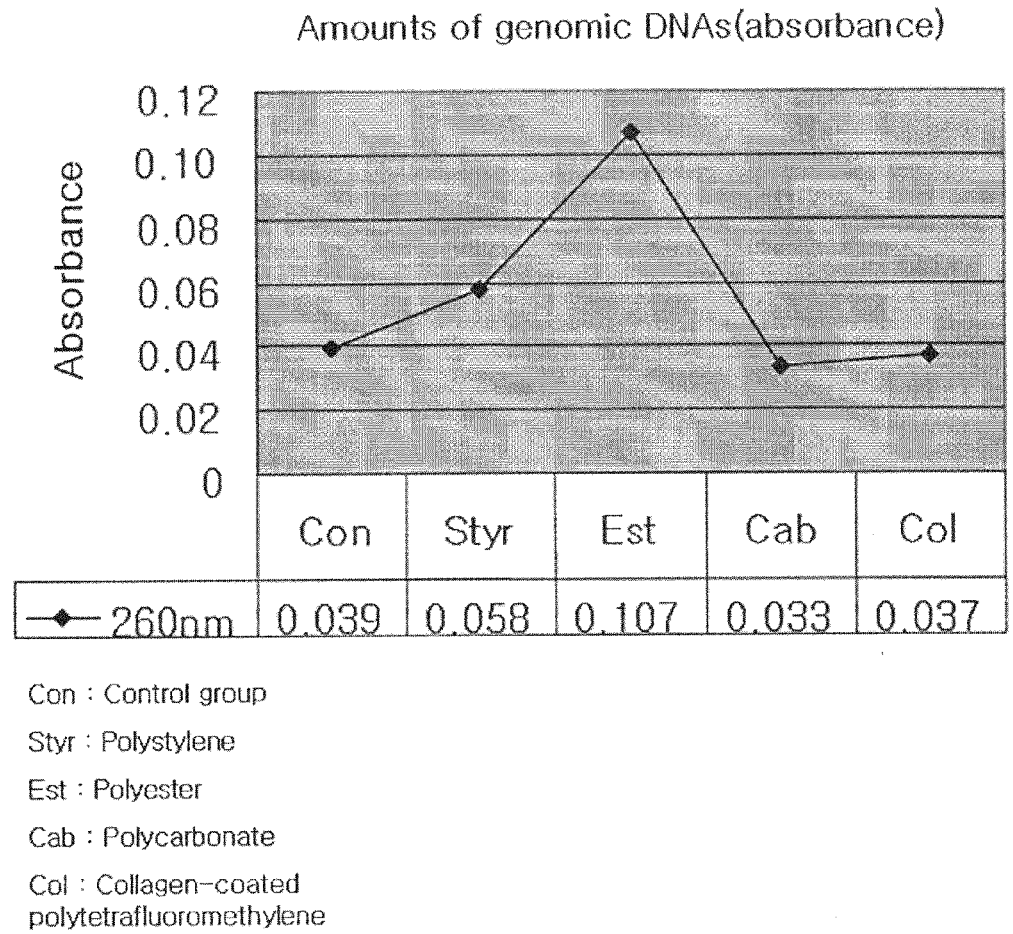
FIG. 6 depicts the amounts of genomic DNAs according to culture conditions that identify the growth of embryonic stem cell HAF6 (72 passages; cultured for 5 days).

Experimental Result 1: Maintenance of Undifferentiation of Stem Cells Co-Cultured by Using Semi-Permeable Membrane In co-cultures using a semi-permeable membrane, the degree of undifferentiation varied according to material attaching stem cells. For example when stem cell and feeder cells were cultured with a border line of polyester membrane, the morphology of stem cells grown on a polystylene culture plate (See FIG. 1; polystylene) was very different from that of stem cells cultured vice versa on a polyester membrane (FIG. 1; polyester) even under the same co-culture condition. The stem cells cultured on a polyester membrane multiplied actively and covered the surface within 5 days erasing the border of colonies (FIG. 6). In a size, stem cells had a high ratio of nuclei and cytoplasm and were crowded, which is a characteristic specific for immature cells. In contrast, the stem cells cultured on a polystylene membrane were attached closely onto the bottom (FIG. 2) without any characteristic of undifferentiation. In the control group cultured on a polystylene membrane, embryonic stem cells were inoculated on feeder cells so that extra-cellular substrates secreted from the feeder cells may be stored between stem cells and polystylene surface. Both the stem cells cultured on a semi-permeable membrane and the control group were identified to remain indifferent by staining with alkaline phosphatase (FIG. 3). But, they were further investigated so as to observe a difference according to culture conditions. The expression of Nanog RNA transcripts as an undifferentiation marker of embryonic stem cell was examined by performing a real-time reverse transcription polymerase chain reaction. As a result, the stem cells on a polystylene had a remarkably lower level that the control group (the number of threshold cycles: control 12.4 vs polystylene 15; FIG. 4). At this moment, the number of threshold cycles is inversely proportional to the amount of particular gene expressed. Therefore, it is proved that both polymer material seeding stem cells and independent space divided by a semi-permeable membrane are important to culture stem cells effectively. Nanog RNA transcripts, an undifferentiation marker of embryonic stem cells was also examined by performing a real-time reverse transcription polymerase chain reaction. As a result, both stem cells on polycarbonate and polytetrafluoroethylene coated with collagen have expressed the transcripts in higher levels than those on polystylene and the control group (FIG. 4).

TABLE 4

Threshold cycles of real-time reverse transcription polymerase chain reaction of Nanog marker

| Groups | Threshold cycle |
|---|---|
| control group | 12.4 |
| Polystylene | 15 |
| Polyester | 11.6 |
| Polycarbonate | 11 |
| collagen-coated polytetrafluoromethylene | 11.7 |

Note)
The number of threshold cycle is inversely proportional to the amount of particular gene expression.

Figure 5:
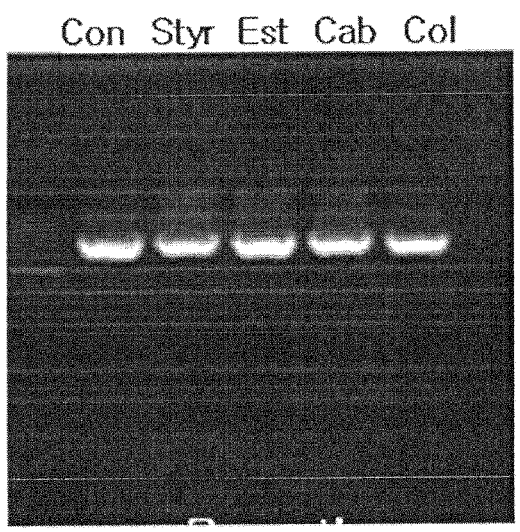
FIG. 5 depicts the expression of RNA transcripts of β-actin, a housekeeping gene; Nanog, an undifferentiation marker of embryonic stem cell HAF6 (72 passages; cultured for 5 days); α-fetoprotein (aFP), an endodermic marker; KDR, a mesodermic marker; and NCAM, an ectodermic marker according to culture conditions by performing a reverse transcription polymerase chain reaction and an agarose gel electrophoresis.
Figure 5:
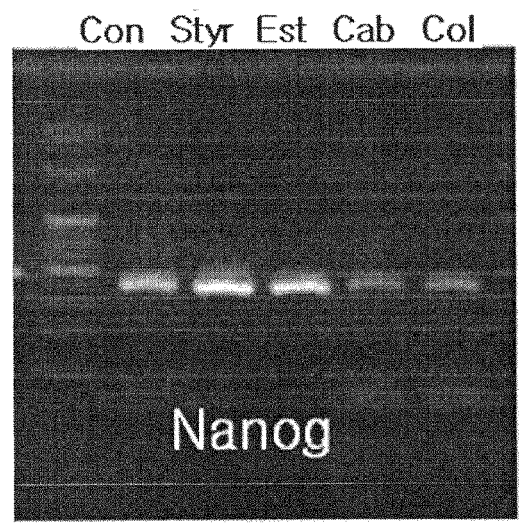
Figure 5:
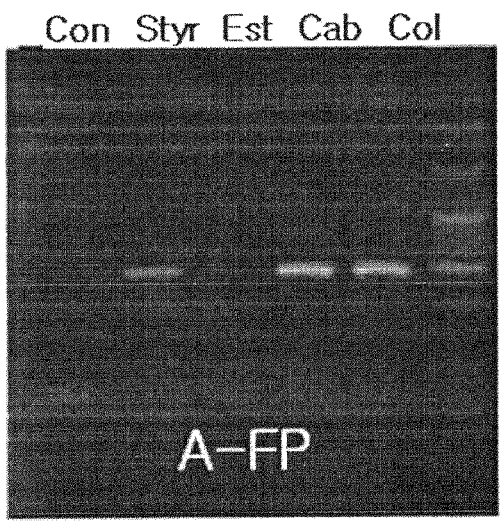
Figure 5:
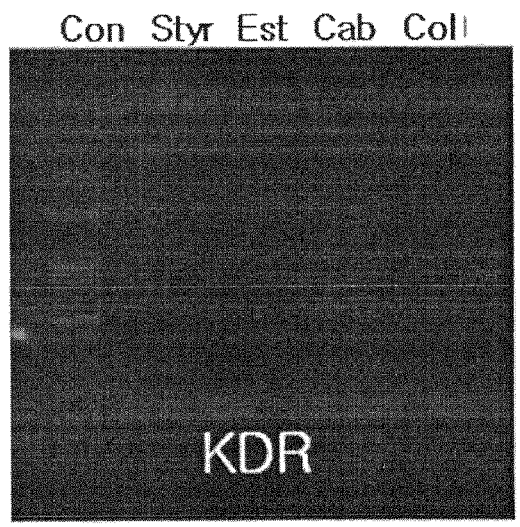
Figure 5:
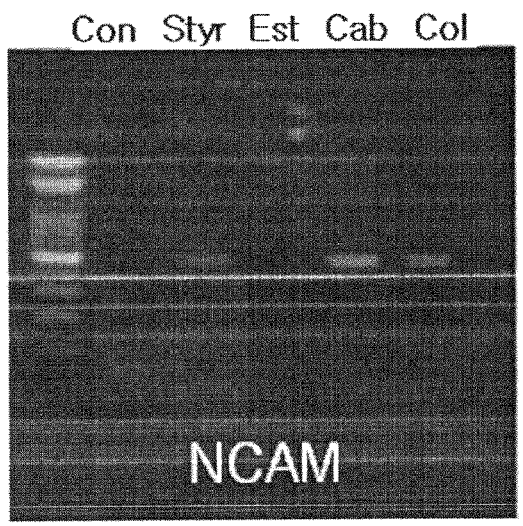

But except for stem cells on a polyester membrane, all the stem cells started to differentiate in α-fetoprotein (aFP) as an endodermic marker and NCAM as an ectodermic marker (FIG. 5). Therefore, it is decided that embryonic stem cells remain indifferent strongly, when co-cultured with feeder cells on a polyester membrane (FIG. 4 and FIG. 5). Because the feeder cells appeared better, this co-culture method is advantageous to give an optimal condition for feeder cells.

Experimental Result 2: Enhancement of Growth Rate of Stem Cells Co-Cultured by Using Semi-Permeable Membrane The growth rates of stem cells were monitored, when co-cultured with a border line of polyester membrane. In detail, the growth rate of stem cells grown on a polystyrene culture plate (See FIG. 1; polystyrene) was very different from that of stem cells cultured vice versa on a polyester membrane (FIG. 1; polyester) even under the same condition. The stem cells cultured on a polyester membrane multiplied actively and fully covered the surface within 5 days erasing the border of colonies (FIG. 6). In contrast, the stem cells cultured on a polystylene did not increase the size of colonies. This result is proved to correspond to the amount of genomic DNAs. In particular, the DNA amount obtained from a polyester membrane increased by about 1.8-fold and further by about 2.7-fold than that of the control group did. Therefore, it is concluded that embryonic stem cells could proliferate most highly, when stem cells were cultured on a polyester membrane and feeder cells on a polystylene plate (FIG. 6).

Figure 7:
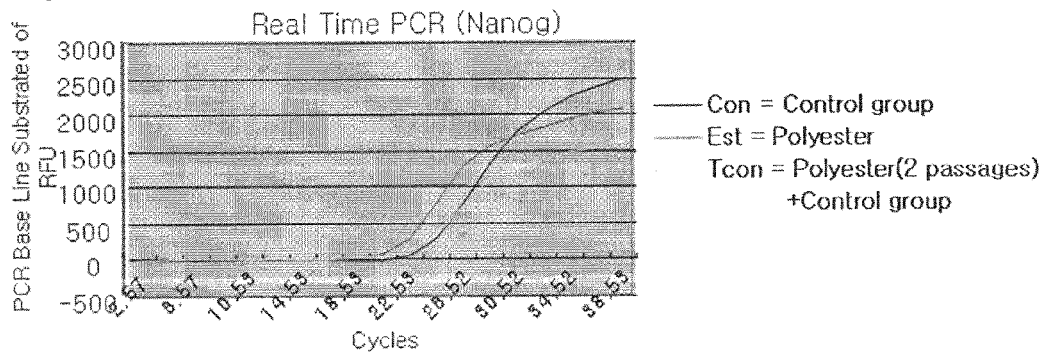
FIG. 7 depicts the expression of Nanog RNA transcripts, an undifferentiation marker of embryonic stem cell HAF6 (72 passages; cultured for 5 days) by performing a real-time reverse transcription polymerase chain reaction.

Experimental Result 3: Examination of Stem Cells Cultured by General Procedure After Co-Cultured on Semi-Permeable Membrane The stem cells were cultured by a general procedure after co-cultured on a semi-permeable membrane. The resulting stem cells were examined whether remaining indifferent increasingly or not. Above all, stem cell and feeder cells were co-cultured with a border line of polyester membrane during 2 passages and then, stem cells were cultured directly on feeder cell through a general culture procedure. As a result, it is observed that the expression of Nanog RNA transcripts of the stem cells should be rather higher than those on a polyester or the control group (FIG. 7) by performing a real-time reverse transcription polymerase chain reaction. The colonies of stem cells also had a cell characteristic of undifferentiation. Therefore, it is proved that the stem cells remain indifferent remarkably even if cultured by a general procedure after co-cultured on a semi-permeable membrane during 1 to 3 passages.

TABLE 5

Threshold cycles of real-time reverse transcription polymerase chain reaction of Nanog marker

| groups | Threshold cycle (Ct) |
|---|---|
| Con | 20.6 |
| Est | 15.5 |
| Tcon | 11 |

Note)
Con is a control group; Est, polyester; and Tcon is polyester (2 passages) + control group.

Experimental Result 4: Examination of Differentiation of Stem Cells Co-Cultured on Semi-Permeable Membrane 3 groups of stem cells including were treated with $10^{-6}$ M of retinoic acid according to culture conditions and analyzed by staining with alkaline phosphatase (FIG. 8). 3 groups were composed of the stem cells cultured on a polyester membrane, the stem cells cultured by a general procedure after co-cultured on a polyester membrane during 2 passages and the control group. As a result, it is observed that all the groups proceed to differentiate after treating retinoic acid and appear negative to alkaline phosphatase. But, the stem cells cultured on a polyester membrane were measured to differentiate in the outer half of colonies and appear positive to alkaline phosphatase in the inner half not to differentiate (FIG. 8). Therefore, it is proved that the stem cells cultured on a polyester membrane might delay a differentiation considerably.

INDUSTRIAL APPLICABILITY

As illustrated and confirmed above, the present invention provides an optimized condition of a stem cell culture, in which stem cells and feeder cells are cultivated independently in separate spaces while permeating essential substances selectively. The stem cells co-cultured in the present invention continue to remain indifferent and be supported by feeder cells until needing being sub-cultured. In addition, the stem cells even for therapeutic use can be obtained without any contaminant since not pretreated by a cytostatic agent such as mitomycin or irradiated. Therefore, the method for co-culturing stem cells by using a membrane of the present invention can be widely used for clinical applications.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A method for culturing human embryonic stem cells with fibroblast feeder cells, in which the human embryonic stem cells and feeder cells are cultivated in two spaces separated by a polyester membrane having a porosity in the range of 2.0 E+06 to 6.0 E+06 pores/cm$^2$, and wherein a greater number of human embryonic stem cells are maintained in an undifferentiated state when compared to human ES cells cultivated using membranes with increased or decreased porosity.

2. The method for culturing human embryonic stem cells according to claim 1, in which the diameter of the pores is in the range of 0.2 to 0.5 μm.

3. The method for culturing human embryonic stem cells according to claim 1, in which the fibroblast feeder cells are cultured under the polyester membrane and the human embryonic stem cells are cultured on the polyester membrane.

4. The method for culturing human embryonic stem cells according to claim 1, in which the feeder cells are cultured with culture media containing serum and the stem cells are cultured with serum-free or serum-replacement media.

5. The method for culturing human embryonic stem cells according to claim 1, in which the feeder cells are not pretreated with any cytostatic agent.

6. The method for culturing human embryonic stem cells according to claim 1, in which the human embryonic stem cells are sub-cultured in a space separated by the polyester membrane and transferred onto fibroblast feeder cells subsequently.

* * * * *